(12) United States Patent
Murphy et al.

(10) Patent No.: US 9,285,355 B2
(45) Date of Patent: Mar. 15, 2016

(54) METHOD AND APPARATUS FOR TESTING LOST CIRCULATION MATERIALS FOR SUBTERRANEAN FORMATIONS

(75) Inventors: Robert J. Murphy, Kingwood, TX (US); Dale E. Jamison, Humble, TX (US); Matthew L. Miller, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 770 days.

(21) Appl. No.: 13/361,755

(22) Filed: Jan. 30, 2012

(65) Prior Publication Data

US 2013/0192358 A1 Aug. 1, 2013

(51) Int. Cl.
*E21B 49/00* (2006.01)
*G01N 33/28* (2006.01)

(52) U.S. Cl.
CPC ........... *G01N 33/2823* (2013.01); *E21B 49/008* (2013.01)

(58) Field of Classification Search
CPC ....... E21B 49/008; E21B 49/00; E21B 49/10; G01N 33/24; G01N 15/0826
USPC ...................................................... 73/152.05
See application file for complete search history.

(56) References Cited

U.S. PATENT DOCUMENTS

| 3,324,712 A | 6/1967 | Smith et al. |
| 8,863,567 B2 * | 10/2014 | Jappy et al. ................ 73/61.64 |
| 2011/0226479 A1 * | 9/2011 | Tippel et al. ............... 166/305.1 |

OTHER PUBLICATIONS

Permeability Plugging Apparatus With 5000 psig Cell Instruction Manual found at https://www.randhsupply.com/Content/Images/uploaded/nivo/New%20Folder/catalog/Catalog/Manuals/Permeability%20Plugging%20Apparatus%20w_5000%20psig%20cell.pdf; 2009 Fann Instrument Company Houston, TX pp. 1-41.*
Loeppke et al., "A Full-Scale Facility for Evaluating Lost Circulation Materials and Techniques", Jan. 1, 1983.
International Preliminary Report on Patentability issued in related PCT Application No. PCT/US2013/022076, mailed Aug. 5, 2014; 8 pages.
"Permeability Plugging Apparatus (PPA)", http:www.fann.com, Oct. 1, 2013, Houston, TX, 2 pages.
"Permeability Plugging Apparatus Instruction Manual—Revision D", http:www.fann.com, Jun. 2013, Houston, TX, 60 pages.
"Lost Circulation, Bridging Materials and the PPA", http:www.fann.com, Jan. 2007, Houston, TX, 2 pages.
Hinkerbein, Thomas E., et al., "Static Slot Testing of Conventional t Lost Circulation Materials", Sandia Report, Jan. 1, 1983, 50 pages.
Abbas, R., et al., "A safety net for controlling lost circulation", Oilfield Review, vol. 15, No. 4 (Nov. 21, 2003), 8 pages.
International Search Report issued in related PCT Application No. PCT/US2013/022076 mailed May 2, 2013, 4 pages.

* cited by examiner

*Primary Examiner* — Hezron E Williams
*Assistant Examiner* — Rodney T Frank
(74) *Attorney, Agent, or Firm* — Scott H. Brown; Baker Botts L.L.P.

(57) ABSTRACT

An apparatus for testing lost circulation materials ("LCMs") for use in a formation is disclosed. The apparatus may comprise a LCM cell that contains at least one formation simulation component. A pressurized tank may be in fluid communication with the LCM cell, and may force a sample LCM slurry into the LCM cell. An LCM receiver may also be in fluid communication with the LCM cell, and may receive the LCM slurry that flows through the LCM cell.

12 Claims, 7 Drawing Sheets

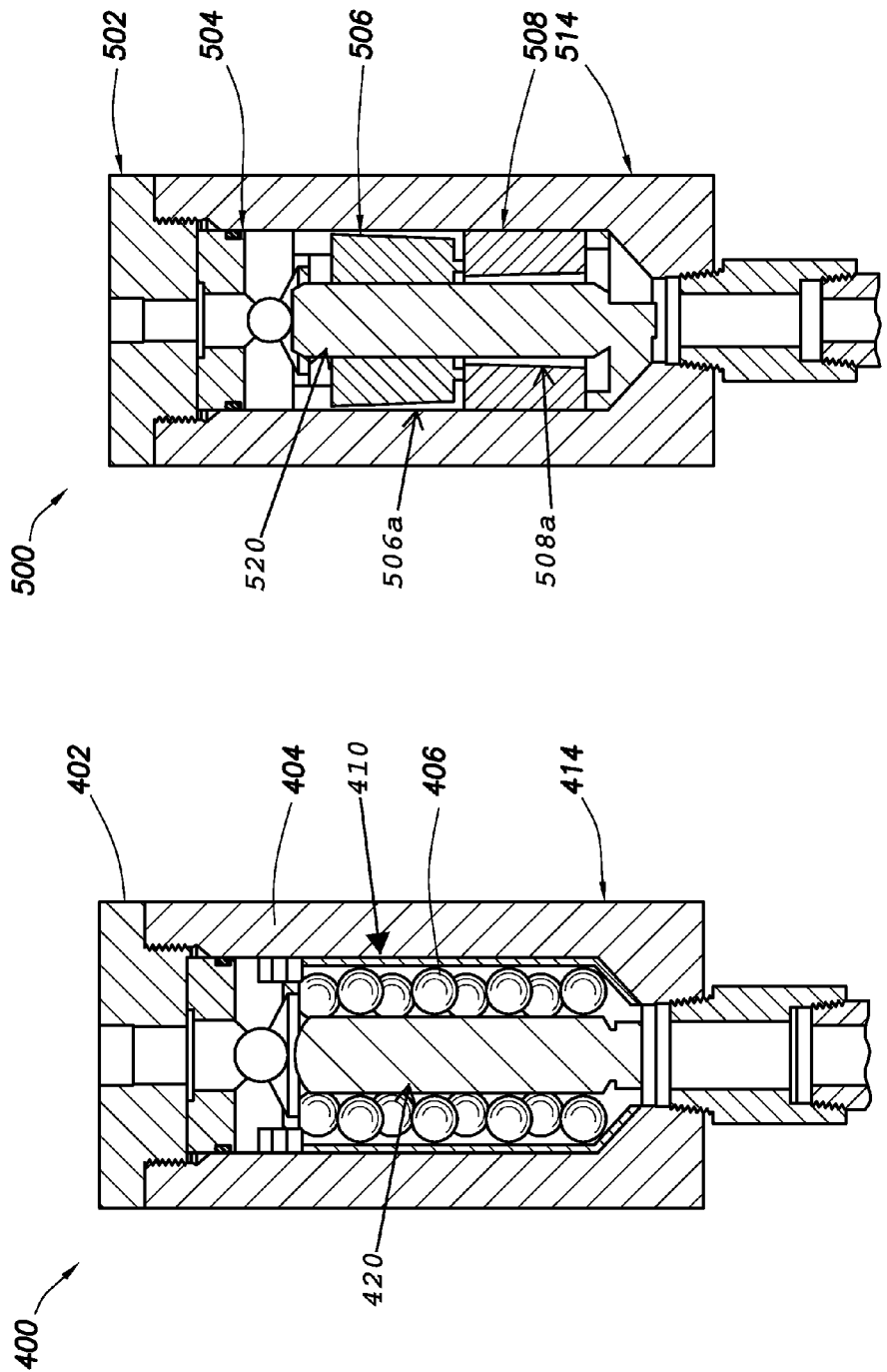

METHOD AND APPARATUS FOR TESTING LOST CIRCULATION MATERIALS FOR SUBTERRANEAN FORMATIONS

BACKGROUND

The present disclosure relates generally to simulating downhole formation characteristics and, more particularly, the present disclosure relates to methods and apparatuses for testing lost circulation materials for subterranean formations.

Subterranean drilling operations typically utilize drilling fluids to provide hydrostatic pressure to prevent formation fluids from entering into the well bore, to keep the drill bit cool and clean during drilling, to carry out drill cuttings, and to suspend the drill cuttings while drilling is paused and when the drilling assembly is brought in and out of the borehole. When drilling into certain formation types, some of the drilling fluid may seep into and become trapped in the formation. This is particularly problematic in vugular formations, which include numerous cavities, known as vugs. If enough drilling fluid is lost to the formation, additional drilling fluid must be introduced into the borehole to maintain drilling efficiency. This can become expensive if large amounts of the drilling fluid are lost.

To prevent drilling fluid loss into vugular formations, lost circulation materials (LCMs) may be added to the drilling fluid. The LCMs typically are typically fibrous (e.g., cedar bark, shredded cane stalks, mineral fiber and hair), flaky (e.g., mica flakes and pieces of plastic or cellophane sheeting) or granular (e.g., ground and sized limestone or marble, wood, nut hulls, Formica, corncobs and cotton hulls) materials. In certain other instances, LCMs may include reactive chemicals which set and harden within the vugs. The LCMs are intended to plug the vugs, preventing the vugs from capturing the fluid portions of the drilling fluid. Unfortunately, testing the effectiveness of LCMs for a particular formation is problematic. For example, current test methods are generally not repeatable, making it difficult to compare the relative effectiveness of two LCMs on the same formation. Additionally, current testing methods cannot accurately model the wide range of vug sizes, particularly the large vugs, needed to simulate vugular formations. As such, what is needed is an apparatus for scalable, repeatable testing of LCMs in vugular formations.

FIGURES

Some specific exemplary embodiments of the disclosure may be understood by referring, in part, to the following description and the accompanying drawings.

FIG. 1 illustrates an example LCM testing system, incorporating aspects of the present disclosure.

FIGS. 2a-g illustrate an example LCM cell and example formation simulation components, according to aspects of the present disclosure.

FIG. 4 illustrates an example LCM cell, incorporating aspects of the present disclosure.

FIG. 5 illustrates an example LCM cell, incorporating aspects of the present disclosure.

While embodiments of this disclosure have been depicted and described and are defined by reference to exemplary embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

The present disclosure relates generally to simulating downhole formation characteristics and, more particularly, the present disclosure relates to methods and apparatuses for testing lost circulation materials for subterranean formations.

Illustrative embodiments of the present disclosure are described in detail herein. In the interest of clarity, not all features of an actual implementation may be described in this specification. It will of course be appreciated that in the development of any such actual embodiment, numerous implementation-specific decisions must be made to achieve the specific implementation goals, which will vary from one implementation to another. Moreover, it will be appreciated that such a development effort might be complex and time-consuming, but would nevertheless be a routine undertaking for those of ordinary skill in the art having the benefit of the present disclosure.

To facilitate a better understanding of the present disclosure, the following examples of certain embodiments are given. In no way should the following examples be read to limit, or define, the scope of the disclosure. Embodiments of the present disclosure may be applicable to horizontal, vertical, deviated, or otherwise nonlinear wellbores in any type of subterranean formation. Embodiments may be applicable to injection wells as well as production wells, including hydrocarbon wells.

Figure 1:
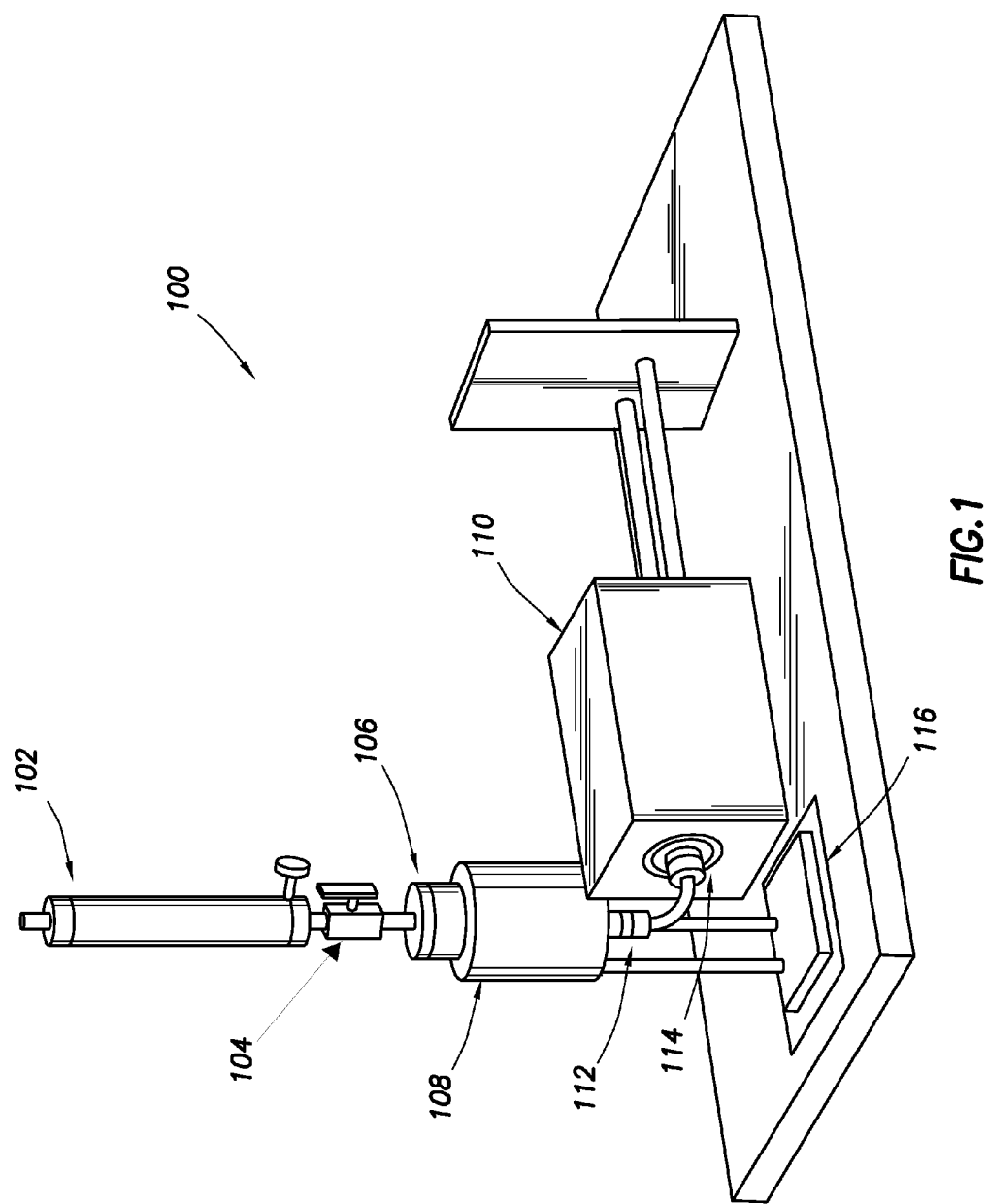

FIG. 1 illustrates an example LCM testing system 100, incorporating aspects of the present disclosure. The LCM testing system 100 includes a pressurized tank, such as permeability plugging apparatus (PPA) cell 114, which may be encased by a heating jacket 110. The heating jacket 110 may heat the contents of the PPA cell 114 to a predetermined temperature. The PPA cell 114 may include an LCM slurry comprising a sample fluid mixed with LCMs. In certain embodiments, the PPA cell 114 may include a floating piston, separating the LCM slurry from a pressurization fluid, which may be a liquid or a gas. The PPA cell 114 may be pressurized by a standard, hand-operated, high-pressure hydraulic pump (not shown). In certain other embodiments, the PPA cell 114 may be pressurized by an automatic mechanism, such as a pneumatic, hydraulic, or mechanical actuator.

The PPA cell 114 may be coupled to a LCM cell 106 through a pipe 112. In some cases a valve (not shown) may be placed between pipe 112 and PPA cell 114 to permit flow control. Connecting the PPA cell 114 with the LCM cell 106 with the pipe 112 may allow for a convenient connection of such a valve, but it is not necessary. In certain embodiments, the PPA cell 114 and LCM cell 106 may be combined into a single unit. The pipe 112 may be any type of high-pressure tubing well known in the art. The pipe 112 may have an inner diameter that is larger than the diameter of a simulated vug in the LCM cell 106, as will be described below. The LCM cell 106 may be at least partially disposed within a heating jacket 108, which may be, for example, a 175 ml high-pressure, high-temperature (HPHT) heating jacket. The heating jacket 108 may be mounted to the ground via a leveling spacer 116, and may heat the LCM cell 106 to a predetermined temperature.

The LCM cell 106 may be coupled to an LCM receiver 102 through a valve assembly 104. In certain embodiments, the LCM receiver 102 may be a HTHP filter press receiver. Each of the PPA cell 114, pipe 112, LCM cell 106, and LCM receiver 102 may be in fluid communication and exposed to similar internal pressures. The valve assembly 104 may couple to the LCM cell 106 through, for example, a threaded connection in a port through a LCM cell cap, as will be discussed below. In certain embodiments, the LCM receiver 102 may be coupled directly to the LCM cell 106 without an intermediate valve 104. In certain embodiments, pressurized gas, typically on the order of 100-200 psig, may be used to provide a formation/back pressure in the LCM receiver 102. The pressurized gas may simulate formation fluid pressure and prevent the boiling of fluids within the LCM cell 106 when the testing temperatures are high.

In operation, the valve assembly 104, LCM cell 106, and pipe 112 may be pre-filled with a fluid suitable to simulate formation fluids. Such fluids would be appreciated by one of ordinary skill in view of this disclosure. The PPA cell 114 may be prefilled with an LCM slurry to be tested. The LCM slurry may include a particular type of LCM at a predetermined concentration and particle size distribution. The heating jackets 108 and 110 may be set to the same temperature for testing. In certain embodiment, the temperature may reflect temperatures seen downhole where the LCM will be used. A pressure may then be imparted on the LCM slurry in the PPA cell 114, forcing the LCM slurry into the pipe 112 and LCM cell 106. The LCM materials may then plug the simulated vugs in the LCM cell 106, creating a back pressure at the PPA cell 114. The effectiveness of the LCM at plugging the simulated vugs in the LCM cell 106 can be measured, for example, by determining the amount of fluid contained within the LCM receiver, determining the amount of pressure the plug can hold from either flow direction, and determining how well the plug stays sealed when pressure is applied from either direction for an extended time at a test temperature. In certain embodiments, the effectiveness of the LCM at plugging the simulated vugs can also be measure by disassembling the LCM cell after a testing, examining the plug formed, and determining its location and composition.

Figure 2B:
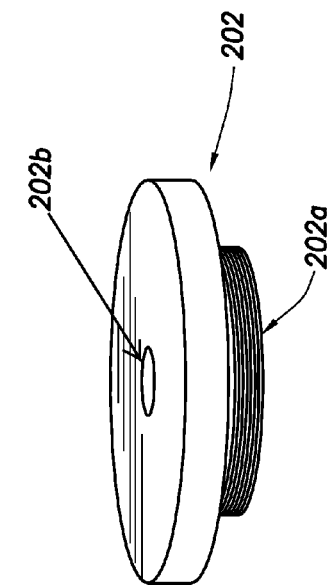
Figure 2C:
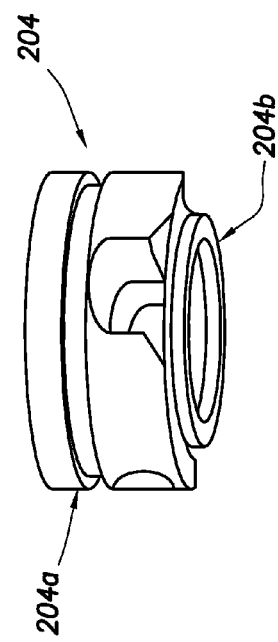
Figure 2A:
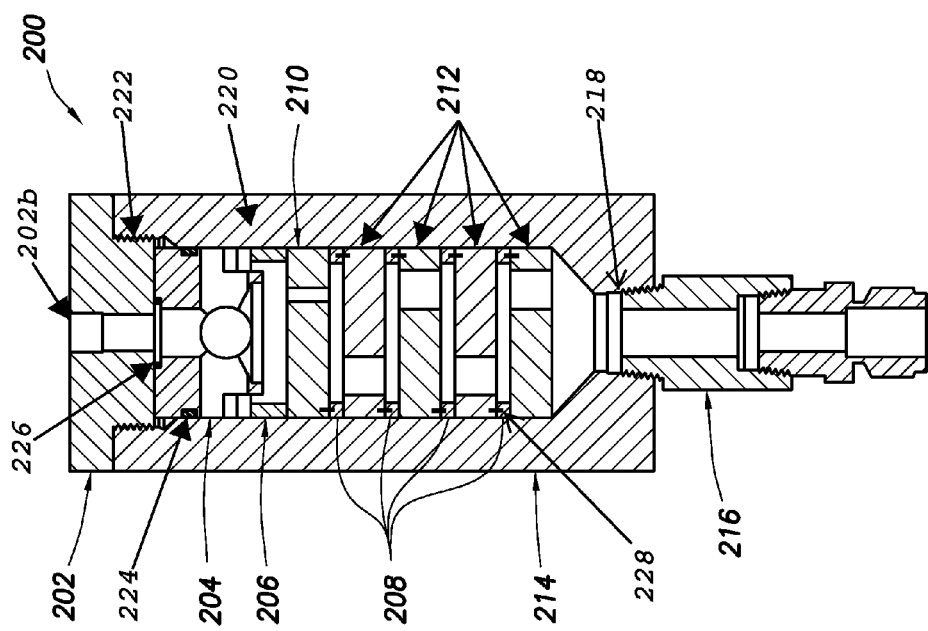

FIG. 2a illustrates an example LCM cell 200, incorporating aspects of the present invention. LCM cell 200 may be incorporated into a LCM testing system such as the LCM testing system illustrated in FIG. 1. For example, the LCM cell 200 may be coupled to a PPA cell through a pipe via connector 216 threadedly engaged with an LCM slurry port 218 positioned at the bottom of the LCM cell housing 214. In certain embodiments, the LCM slurry port 218 may have an effective internal diameter of about ½ inch. Although the connector 216 is shown threadedly engaged with the LCM slurry input port 218, other connection means are possible, provided the connection means are rated to withstand the pressure generated at a PPA cell.

As will be appreciated by one of ordinary skill in the art in view of this disclosure, the LCM cell may be used to simulate multiple subterranean formations. Although the following disclosure will primarily discuss the simulation of vugular formations, the simulation of other formation types and formation characteristics are possible. For example, as will be discussed below, the LCM cell may be configured to simulate non-vugular lost circulation situations like fractures and porosity. Accordingly, the configuration of an LCM cell to simulate a vugular formation should not be seen as limiting.

The LCM cell housing 214 may be generally cylindrical, and may form an generally cylindrical internal cavity 220 with a taper at one end. The internal cavity 220 may be open at an upper end of the housing 214. In certain embodiments, the cylindrical portion of the internal cavity 220 may have a diameter of 2 inches, and taper down to ½ inch at the LCM slurry port 218. In certain embodiments, as shown in FIG. 2a, the LCM cell housing 214 includes threads within the LCM slurry input port 218. The LCM cell may also include threads 222 to engage with a LCM cell cap 202. As can be seen in FIG. 2b, the LCM cell cap 202 may include complementary threads 202a to removeably engage with threads at the top of the LCM cell housing 214. The LCM cell cap 202 may also include a port 202b extending axially through the LCM cell cap 202. The port 202b may be sized to allow the passage of small LCM particles, and may have an effective internal diameter of ¼ inch. The port 202b may include internal threads and may be connected, for example, to an LCM receiver or valve mechanism through the threaded connection, and may provide fluid communication between the internal cavity of the LCM cell 200 and an LCM receiver.

In certain embodiments, the LCM cell cap 202 may not include a sealing mechanism. In the embodiment shown in FIG. 2a, a retainer 204 may be located inside the LCM cell 200, below the LCM cell cap 202, and may seal the internal cavity of the LCM cell 200. The retainer 204 may include seals 224 and 226 to prevent any fluids inside the LCM cell from escaping through the threaded connection of the LCM cell cap 202. As can be seen in FIG. 2c, the retainer 204 may include a groove 204a on an outer face and a groove one top surface (not shown) in which an o-ring type seal may be disposed. Other sealing mechanisms are possible, as are multiple seals, as would be appreciated by one of ordinary skill in the art in view of this disclosure. The outer diameter of the retainer 204 may be substantially similar to the diameter of the inner cavity of the LCM cell 206. The retainer 204 may be inserted into the LCM cell 200, causing the o-ring 224 to engage with the inner cavity 220 of the LCM cell 200. The retainer 204 may also include at least one internal port 204b through which formation fluids may pass from the LCM cell into an LCM receiver coupled to the LCM cell 200.

The LCM cell 202 may further include formation simulation components that may be used to simulate vugular formations, or other non-vugular formations, in both a scalable and repeatable way. For example, the interior cavity 220 of the LCM cell 200 may be filled with stacked formation simulation components containing flow passages. In the embodiment shown in FIG. 2, the formation simulation components may comprise plates and plate spacers. The plates and plate spacers, shown in FIG. 2 may include vug plates 210 and 212, and vug plate spacers 208, as they include flow passages adapted to simulate vugular formations, as will be described below. As can be seen in FIG. 2a, the vug plates 210 and 212 and vug plate spacer 208 may have an effective diameter equal to the diameter of the inner cavity 220 of the LCM cell 200, and may be stacked within the inner cavity 220. In certain embodiments, the vug plates 210 and 212 and vug plate spacer 208 may be held in position by the retainer 204 and LCM cell cap 202, instead of engaging with the inner cavity 220 of the LCM cell 200 to prevent movement. In certain embodiment the plates, 208 and 212, and spacers 208, may be oriented relative to each using a pin and receiver configuration. In one embodiment, as is shown in FIG. 2, a pin 228 may fit into a receiver in both an adjacent plate and spacer, aligning the plate and spacer rotationally. In certain other embodiments (not shown) the pin may be integrated into a plate or spacer, with the adjacent plate or spacer including a corresponding receiver.

Figure 2D:
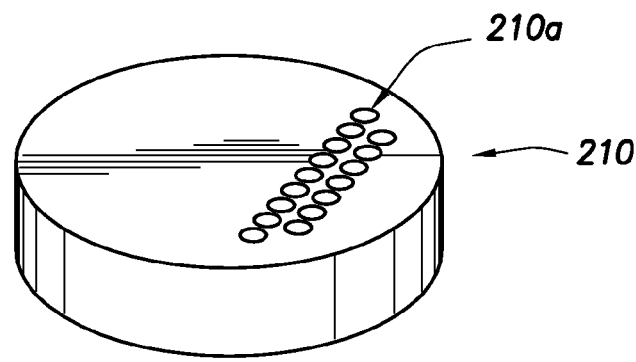

FIG. 2d illustrates a close up view of vug plate 210. As can be seen, vug plate 210 is a cylindrical plate comprising staggered holes 210a extending through the thickness of the vug plate 210. In certain embodiments, all vug plates used within a LCM cell may have the same thickness, such as ½ inch. The staggered holes 210a comprise 16 holes, each having a diameter of ⅛ inch, providing an overall hole area size of 0.1963 inches squared. As can be seen, each of the holes 210a may have square edges, but there are many other configurations for holes and passages that would be appreciated by one of ordinary skill in view of this disclosure.

Figure 2E:
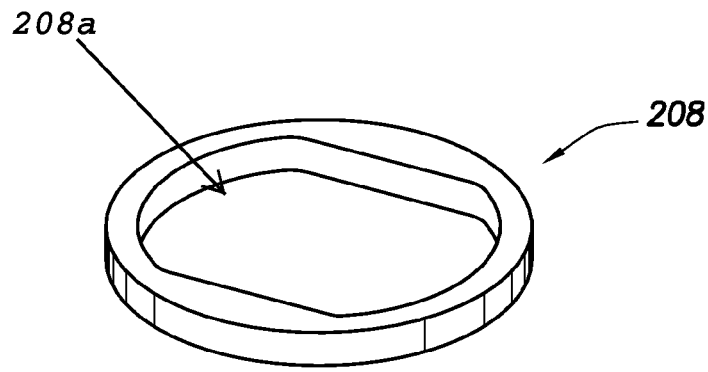
Figure 2F:
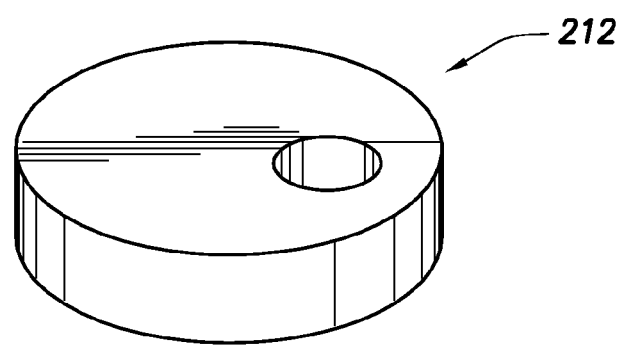

In contrast, FIG. 2f illustrates a close up view of vug plate 212. Like vug plate 210, vug plate 212 may have a thickness of ½ inch. Unlike vug plate 210, however, vug plate 212 comprises a single hole with an effective diameter of ½ inch. Notably, the overall hole area size of the vug plate 212 is 0.1963 inches squared, the same as the overall hole area size of the vug plate 210. In certain embodiments, each vug plate stacked in a LCM cell may have the same overall hole area size. This ensures generally equal flow of fluids through the LCM cell and the effective simulation of a vugular formation. Other embodiments of a vug plate may include, for example, four holes with an effective diameter of ¼ inch, maintaining the overall hole area size of 0.1963 inches squared. Other configurations may utilize hole sizes such that the overall hole area size is not 0.1963 inches squared. Notably, each of the holes through the vug plate may simulate a vug within a vugular formation having a size similar to the hole area size of the corresponding hole. Accordingly, different vugular formations may be simulated by selecting hole sizes that correspond to the vugular formation of interest. Because the vug plates, for example, can accommodate a wide variety of hole sizes, a wide range of vugular formations can be simulated.

FIG. 2e illustrates an example vug plate spacer 208, according to aspects of the present disclosures. As can be seen, the vug plate spacer 208 comprises a ring structure that defines an interior opening 208a. The configuration of the vug plate spacer 208 may be modified depending on the placement of the holes in an adjacent vug plate, so as to not restrict the flow of fluid through the vug plates. For example, if the holes of the vug plate are spaced further apart than the holes 210a in LCM cell 210, the interior opening may be widened such that the structure of the vug plate spacer does not overlap with a hole in the adjacent vug plate. Likewise, if the holes are closer together, the interior opening may be narrowed.

Figure 2G:
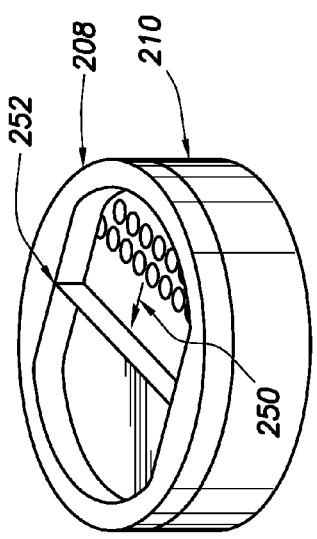

In certain embodiments, a vug plate spacer may be designed such that a flow cross-sectional area of the vug plate spacer is approximately the same as the overall hole area size of the adjacent vug plates. FIG. 2g illustrates an example vug plate spacer 208 stacked on top of an example vug plate 210. Formation fluids may flow from the vug plate holes along path 250, into the interior opening of the vug plate space 208. The flow cross-sectional area 252 of the vug plate spacer 208 is defined by the thickness of the vug plate spacer 208 and the width of the interior opening of the vug plate spacer, and the flow cross-sectional area can be modified by altering either variable. For example, if the interior opening needs to be wider to accommodate a certain hole placement, the thickness of the vug plate spacer can be decreased to maintain a constant flow cross-sectional area. In the embodiment shown in FIG. 2g, the flow cross-sectional area may be 0.1963 inches squared to match the overall hole area size of the adjacent vug plate 210.

In certain embodiments, a LCM cell may include vug plates with different hole sizes and placement. For example, LCM cell 200 includes four vug plates similar to vug plate 212, with a single ½ inch diameter hole, and a single vug plate 210 with multiple ⅛ inch holes. The present configuration is advantageous because it may cause a LCM that passes through the vug plates similar to vug plate 212 to be captured at vug plate 210 before passing into and possibly clogging the LCM receiver. Other configurations are possible, as would be appreciated by one of ordinary skill in the art in view of this disclosure. For example, the LCM cell may be populated with only three vug plates instead of two, or a different vugular formation simulation component entirely.

Depending on the configuration, the vugular formation simulation components inside of a LCM cell may have different total heights. For example, if one layer of the vug plates and vug plate spacers is removed from the LCM cell 200 in FIG. 2a, the overall height of the stacked formation simulation components will be smaller. To accommodate various configurations of vugular formation simulation components, a variable spacer 206 may be inserted between the retainer 204 and the vugular formation simulation components. The variable spacer 206 may be, for example, a stack-up spacer, with variable thickness, that can be inserted at the top of the stack so that the height of the stack remains constant across different configurations. The constant height of the stack ensures that the installation of the LCM cell cap 202 and retainer 204 compresses the stack and holds the formation simulation components in position. This is advantageous because it may allow repeatability of testing and scalability of the vugular formation simulation components placed within the LCM cell.

Figure 3:
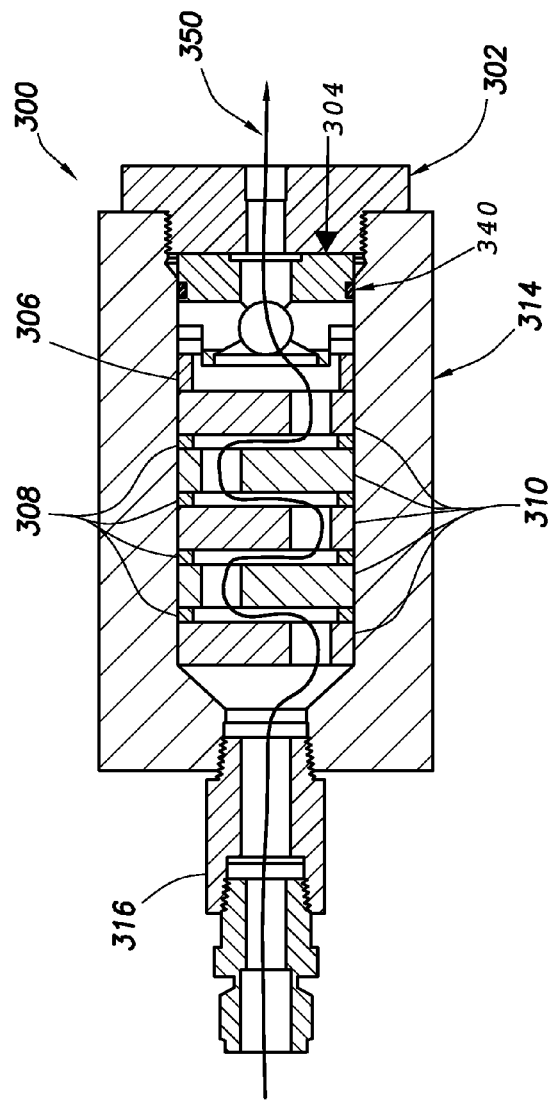
FIG. 3 illustrates a flow path through an example LCM cell, according to aspects of the present disclosure.

FIG. 3 illustrates an example flow pattern 350 through a LCM cell 300. As can be seen, an LCM slurry may pass through the LCM slurry port 316 and into an inner cavity of LCM cell 300, defined by the LCM cell housing 314. The LCM slurry may pass through a vug plate 310 before entering the interior opening of a vug plate space 308. The LCM slurry may then pass laterally through the interior opening of the vug plate spacer 308, encountering the flow cross-sectional area of the vug plate spacer 308, as described above. The LCM slurry may proceed in a serpentine fashion through the LCM cell 300, past the variable spacer 306, into the retainer 304 with seal 340 and out of a port in the LCM cell cap 302. In certain embodiments, the overall hole area size/flow cross sectional area of every vug plate and vug plate spacer may be approximately the same. This allows for a generally even flow through the LCM cell 300.

Although formation simulation components described thus far have included plates and plate spacers, other formation simulation components are possible. For example, FIG. 4 illustrates a LCM cell 400 comprising ⅜ inch diameter balls 406 arranged in an annular inner cavity positioned between the an LCM cell housing liner 410 and a cylindrical inner structure 420. The formation simulation components shown in FIG. 4 may also be used to simulate vugular formations, in a manner similar to the LCM cell configuration shown in FIG. 2. The dimensions of the LCM cell housing liner 410 and the cylindrical inner structure 420 configure the internal diameter of the LCM cell housing 414 so that each layer of balls forms a ring around the cylindrical structure 420 with no gaps. The arrangement of balls assures that each test will be conducted with the same number of balls in the same pattern. Other sizes of balls are possible, as would be appreciated by one of ordinary skill in the art in view of this disclosure. The balls 406 may be placed within the annular inner cavity and held in place by the LCM cell cap 402 and retainer 404, which may be similar to the LCM cell cap 202 and retainer 204 discussed above. Depending on the vugular formation to be simulated in the LCM cell, and the testing parameters, the balls 406 may be stacked at various heights within the LCM cell 400. Accordingly, a variable spacer may be used to ensure that the LCM cell cap 402 and retainer 404 imparts sufficient compression on the balls to hold them in place.

In another embodiment, as illustrated in FIG. 5, the formation simulation components may comprise two annular inserts 506 and 508 disposed within the LCM cell housing 514 of LCM cell 500. The LCM configuration in FIG. 5 may also be used to simulate vugular formations. The annular inserts may be arranged coaxially with an internal cylindrical structure 520 of the LCM cell 500 similar to the structure shown in FIG. 4. The annular inserts 506 and 508 may be configured such that when installed they create tapered slots within the LCM cell 500. For example, annular insert 508 includes an outer cylindrical surface approximately the same diameter as the inner surface of the LCM cell housing 514. The interior surface of annular insert 508 is tapered and greater at all points that the diameter of the internal cylindrical structure of the LCM cell 500. When installed, the annular insert 508 creates a tapered slot 508a for the LCM slurry to flow, narrowing as it gets further from the LCM slurry port. Annular insert 506 may include spacers at the bottom to stack on top of annular insert 508. The annular insert 506 includes an interior cylindrical surface that is approximately the same diameter as the inner cylindrical structure 520 of the LCM cell 500. The exterior surface of the annular insert 506 may create a tapered slot 506a, with the diameter of the annular insert 506 increasing as it gets further from annular insert 508. The flow area of the tapered slots 506a and 508a created by annular inserts 506 and 508, and the flow area between annular inserts 506 and 508 created by the spacers, may be designed to be approximately the same, as described above. Notably, the tapered slots created by the annular inserts 506 and 508 may simulate a vugular formation, with a size approximately the same as the flow area of the tapered slots.

Figure 6:
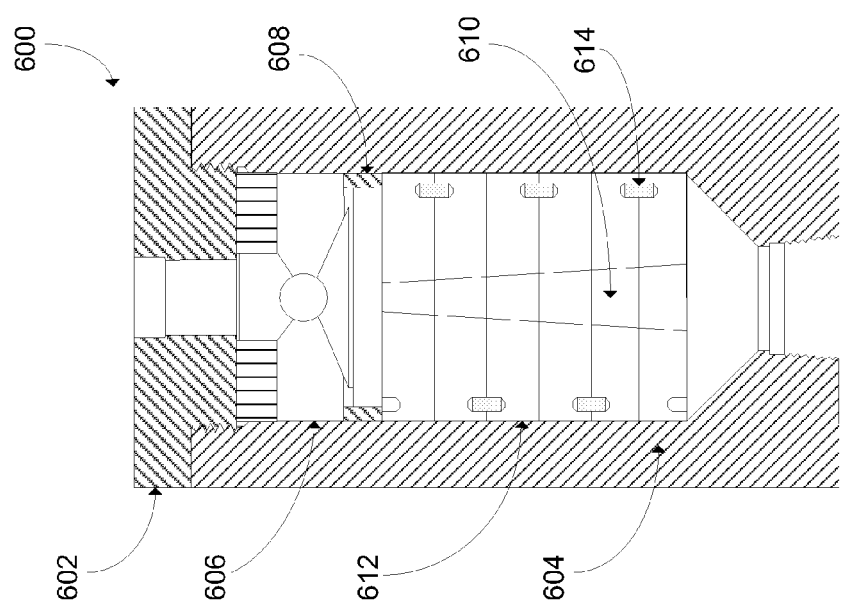
FIG. 6 illustrates an example LCM cell, incorporating aspects of the present disclosure.

In another embodiment, as illustrated in FIG. 6, the formation simulation components may comprise stacked plates forming a tapered slot. The stacked plates, referred to collectively as 612, may each include a portion of a tapered slot 610, and may be aligned within the LCM cell 600 using pins, referred to collectively 614, to form the entire tapered slot 610. As can be seen, the plates 612 may be sized to fit within the inner cavity of a LCM cell housing 604. As can also be seen, the plates 612 may be retained within the LCM cell using stacked spacers 608, retainer 606 and LCM cap 602. In certain embodiments, formation simulation components similar to plates 612 may be used to simulate a fracture within a subterranean formation, therefore allowing tests to determine the effectiveness of LCMs on plugging a fracture.

Figure 7:
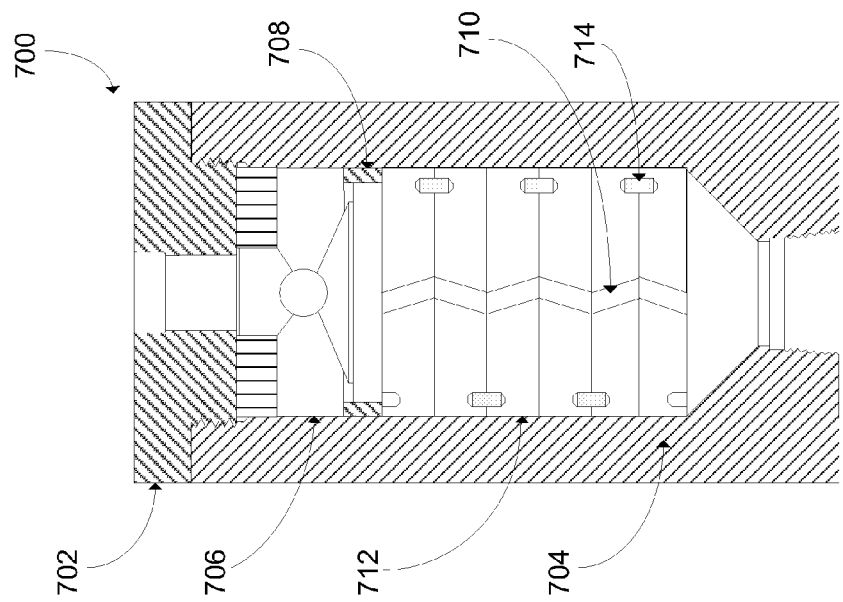
FIG. 7 illustrates an example LCM cell, incorporating aspects of the present disclosure.

In another embodiment, as illustrated in FIG. 7, the formation simulation components may comprise stacked plates forming a zig-zagged slot. The stacked plates, referred to collectively as 712, may each include a portion of a zig-zagged slot 710, and may be aligned within the LCM cell 700 using pins, referred to collectively 714, to form the entire zig-zagged slot 710. As can be seen, the plates 712 may be sized to fit within the inner cavity of a LCM cell housing 704. As can also be seen, the plates 712 may be retained within the LCM cell using stacked spacers 708, retainer 706 and LCM cap 702. In certain embodiments, formation simulation components similar to plates 712 may be used in LCM or vugular formation plugging studies.

Figure 8:
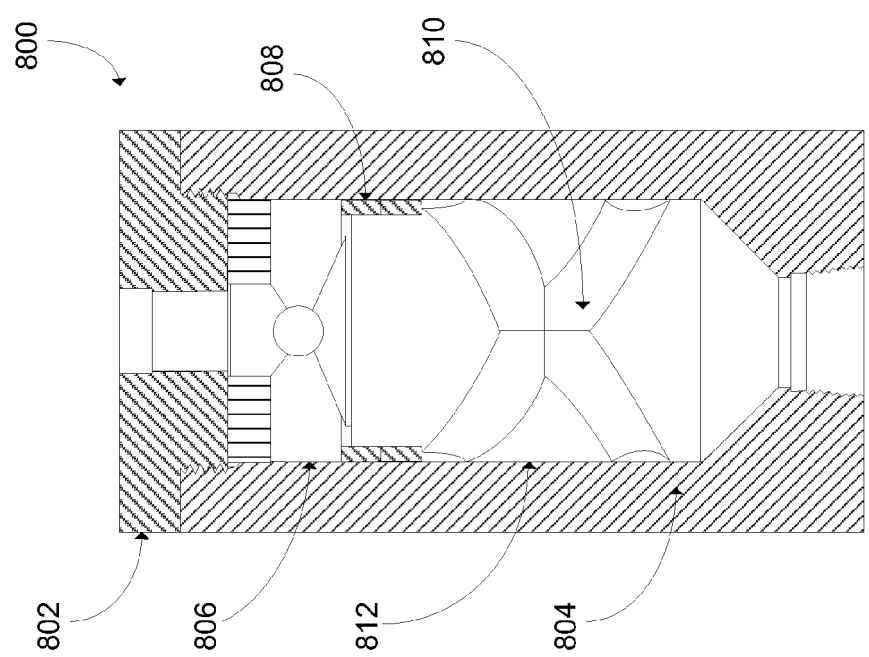
FIG. 8 illustrates an example LCM cell, incorporating aspects of the present disclosure.

In another embodiment, as illustrated in FIG. 8, the formation simulation component may comprise an insert 812 containing a double helix grove pattern 810 machined on an exterior surface. As can be seen, the insert 812 may be sized to fit within the inner cavity of a LCM cell housing 804. As can also be seen, the insert 812 may be retained within the LCM cell using stacked spacers 808, retainer 806 and LCM cap 802. In certain embodiments, an insert similar to insert 812 may be used to simulate a vugular formation. The grooves in the groove pattern 810 may have the same cross-sectional area of a half inch hole, similar to those within the LCM described with respect to FIG. 2. Many other groove shapes and pitches are possible.

Although some example embodiments of formation simulation components are described above, the formation simulation components are not limited to the embodiments. Rather, other configurations fall within the scope of this disclosure. Notably, the embodiments described herein and other configurations can be combined and modified as needed to simulate a vugular formation. Such combinations and modifications may accomplish similar results to the embodiments described herein by providing a flow path through the vugular cell that is repeatable, scalable, and capable of accounting for LCM materials of differing sizes.

Returning to FIG. 1, a typical test procedure utilizing an LCM testing system similar to LCM testing system 100 may proceed as described below. The LCM cell may be assembled without the LCM cell cap or retainer. This may include positioning the formation simulation components with an inner cavity of the LCM cell. The PPA cell 110 may be loaded with sample LCM slurry by moving an internal piston to the bottom, thus creating room to load the LCM slurry, filling the PPA cell with the slurry, and closing and sealing the PPA cell without a filtration disk, which would otherwise filter out the LCM. Once closed, the LCM slurry level in the PPA cell can be topped off.

A ⅝ inch tube, similar to tube 112 in FIG. 1, may be connected to the PPA cell. The PPA cell may then be placed in a heating jacket, such as a 500 ml horizontal heating jacket, with the tubing end up. The LCM cell may also be connected to a heating jacket, such as a 175 ml Heating Jacket, and the ⅝ inch tube may be connected to the bottom of the LCM cell. A pump may be connected to the PPA cell with the pump pressure release valve open to prevent the LCM from discharging from the PPA cell. In certain embodiments, the pump may be a manual hydraulic pump, while in other it may be an automatic hydraulic pump, or a different type of pump, as would be appreciated by one of ordinary skill in view of this disclosure.

The LCM cell may be filled with a simulated formation fluid and sealed by inserting a retainer and capping the LCM cell by screwing on a LCM cell cap. The LCM receiver may be connected to the LCM cell, and the LCM receiver may be filled through an LCM receiver cap with the same simulated formation fluid used to fill the LCM cell. Excess air may be removed from the system using a mild vacuum at the LCM receiver, and the LCM receiver may be pressurized to the back-pressure required for the testing procedure. The back-pressure may reflect the pressure at the vugular formation being simulated in the test. Any excess simulated formation fluid may be drained from the LCM receiver.

Both of the heating jackets—for the LCM cell and the PPA cell—may be heated to the test temperature. The test temperature may reflect the temperature of the vugular formation being simulated in the test. After a predetermined amount of time to allow the temperature to stabilize, such as 30 minutes, the LCM receiver may be drained. After the LCM receiver is drained, the pump pressure release vale can be closed. Rapid pumping may then push the LCM slurry from the PPA cell into the LCM cell until a test pressure is reached. The test pressure may comprise the pressure which the drilling fluids may exert on the vugular formation. Once the test pressure have been reached, the LCM receiver may be drained to determine the volume of fluid drained.

Each of the above steps may be completed manually. In certain embodiments, some or all of the steps may be automated. For example, pressurizing the PPA cell and the LCM receiver may be accomplished using hand pumps or automatic pumps set to a desired pressure.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Also, the terms in the claims have their plain, ordinary meaning unless otherwise explicitly and clearly defined by the patentee. The indefinite articles "a" or "an," as used in the claims, are defined herein to mean one or more than one of the element that it introduces.

What is claimed is:

1. An cell for testing lost circulation materials (LCM) used in a formation, comprising:
    a housing, wherein the housing defines an internal cavity;
    at least one vugular formation simulation component positioned within the internal cavity, wherein the at least one formation simulation component comprises balls positioned between a cylindrical inner structure and a housing liner disposed within the internal cavity;
    a retainer positioned above the at least one formation simulation component in the internal cavity; and
    a cap removably engaged with the housing, wherein the cap compresses the at least one formation simulation component and the retainer within the internal cavity when engaged.

2. The cell of claim 1, further comprising a first port within the housing providing fluid communication with the internal cavity; and a second port within the cap providing fluid communication with the internal cavity.

3. The cell of claim 1, further comprising a variable spacer positioned within the internal cavity.

4. The cell of claim 1, wherein the balls are characterized by ⅜ inch diameters.

5. An cell for testing lost circulation materials (LCM) used in a formation, comprising:
    a housing, wherein the housing defines an internal cavity;
    at least one vugular formation simulation component positioned within the internal cavity, wherein the at least one formation simulation component comprises at least one annular insert positioned around a cylindrical inner structure disposed within the internal cavity;
    a retainer positioned above the at least one formation simulation component in the internal cavity; and
    a cap removably engaged with the housing, wherein the cap compresses the at least one formation simulation component and the retainer within the internal cavity when engaged.

6. The cell of claim 5, further comprising a first port within the housing providing fluid communication with the internal cavity; and a second port within the cap providing fluid communication with the internal cavity.

7. The cell of claim 5, wherein the at least one annular insert comprises a tapered inner surface.

8. The cell of claim 5, wherein the at least one annular insert comprises a tapered outer surface.

9. The cell of claim 5, wherein the at least one annular insert positioned around a cylindrical inner structure disposed within the internal cavity comprises two coaxially-arranged annular inserts.

10. The cell of claim 9, wherein one of the two coaxially-arranged annular inserts comprises a tapered inner surface and the other of the two coaxially-arranged annular inserts comprises a tapered outer surface.

11. The cell of claim 10, further comprising at least one spacer positioned between the two coaxially-arranged annular inserts.

12. The cell of claim 11, wherein a flow area defined, in part, by the tapered inner surface, a flow area defined, in part, by the tapered outer surface, and a flow area defined, in part, by the at least one spacer is approximately the same.

* * * * *